United States Patent [19]

Smith

[11] 4,157,771

[45] Jun. 12, 1979

[54] BAG COMPRESSING DEVICE FOR DISPENSING FLUID

[75] Inventor: Edward M. Smith, Pike Township, Knox County, Ohio

[73] Assignee: The Gorman-Rupp Company, Mansfield, Ohio

[21] Appl. No.: 840,314

[22] Filed: Oct. 7, 1977

[51] Int. Cl.[2] .............................................. B65D 35/28

[52] U.S. Cl. .................................... 222/103; 100/265; 128/DIG. 12; 222/340; 222/390

[58] Field of Search .................... 128/214 F, DIG. 12; 100/265; 74/520; 312/71; 221/279; 222/103, 105, 336, 340, 390

[56] References Cited

U.S. PATENT DOCUMENTS

| | | | |
|---|---|---|---|
| 3,625,401 | 12/1971 | Terry | 222/103 |
| 3,902,635 | 9/1975 | Jinotti | 222/103 |
| 4,033,479 | 7/1977 | Fletcher et al. | 128/DIG. 12 |

FOREIGN PATENT DOCUMENTS

| | | | |
|---|---|---|---|
| 2323762 | 11/1974 | Fed. Rep. of Germany | 222/105 |

OTHER PUBLICATIONS

"Toggle Linkage Applications in Different Mechanisms", Product Engineering, Annual Handbook of Product Design of 1953, pp. F26, 27.

*Primary Examiner*—David A. Scherbel
*Attorney, Agent, or Firm*—Hamilton, Renner & Kenner

[57] ABSTRACT

A device for feeding fluid at substantially constant pressure from a flexible container compressible by a pressure plate movable toward and away from a stationary plate to form a variable volume chamber for the container. A linkage connects the pressure plate to spaced-apart transverse tensioning plates attached to the ends of a tensioning spring. The spring encircles a screw having threaded oppositely portions with nuts thereon for spreading the tensioning plates apart to tension the spring and move the pressure plate away from the stationary plate when the screw is rotated in one direction, and the tensioning plates are axially retractable on the screw by spring tension when the nuts are retracted by reversely rotating the screw, to apply substantially constant closing pressure through the linkage to the pressure plate.

5 Claims, 4 Drawing Figures

BAG COMPRESSING DEVICE FOR DISPENSING FLUID

BACKGROUND OF THE INVENTION

U.S. Pat. No. 3,565,292 discloses a fluid feeding device in which a movable piston is biased directly by a compression spring to move away from a stationary plate and compress a fluid bag for feeding fluid therefrom, and a screw extending vertically from the piston through the stationary plate has a handle threaded on the screw and bearing against the exterior of the stationary plate. Rotating the handle in one direction moves the piston toward the stationary plate and compresses the spring, and rotating the handle in the opposite direction allows the piston to move away from the stationary plate by spring action to compress the bag. A disadvantage of this device is that as the bag is compressed the spring pressure decreases and varies the rate of fluid flow, and it is very important in feeding blood to a patient, for example, to maintain the fluid flow substantially constant.

SUMMARY OF THE INVENTION

It is an object of the present invention to provide an improved fluid pressurizing device which applies substantially constant pressure to a fluid container for feeding fluid therefrom at a substantially constant rate.

Another object is to provide an improved fluid pressurizing device utilizing a spring in combination with a mechanical linkage such that the decreasing force of the spring is substantially compensated by the mechanical advantage of the linkage.

A further object is to provide a fluid pressurizing device having a pressure plate movable toward a flexible container by a tension spring connected to the pressure plate by a linkage which compensates for decreasing tension of the spring as the container is compressed.

A still further object is to provide an improved fluid pressurizing device which accomplishes the foregoing objectives in a simple, compact and inexpensive apparatus.

These and other objects are attained by the present invention which is disclosed in the accompanying drawings and described in the following specification as exemplifying the best known mode of carrying out the invention. Various modifications and changes in details of construction are included within the scope of the appended claims.

DESCRIPTION OF A PREFERRED EMBODIMENT

Figure 1:
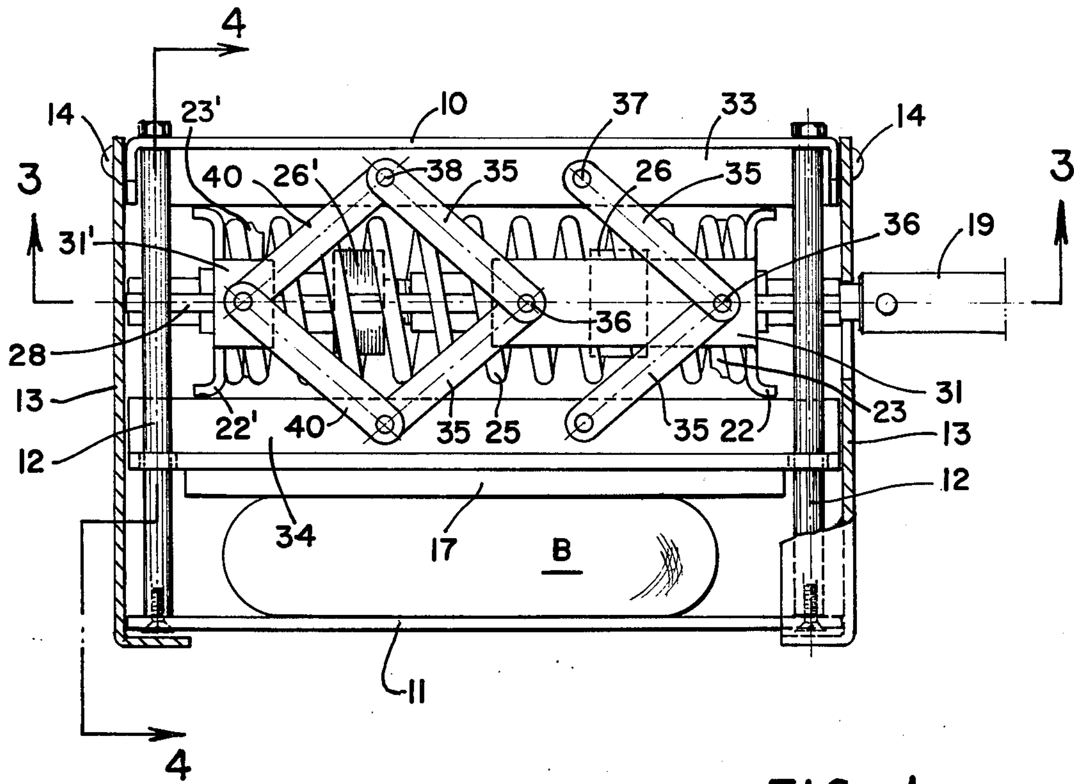
FIG. 1 is a sectional view on line 1—1 of FIG. 3 of the improved device with the pressure plate moved away from the stationary plate to allow insertion of the fluid container between the plates.

The improved fluid pressurizing device preferably has a rectangular top plate 10 and a rectangular bottom plate 11 rigidly connected together by four tie bolts 12 at the corners. A housing is preferably provided having end plates 13 secured to the top plates by screws 14 and side plates 15 secured to the end plates.

A pressure plate 17 is located above the bottom plate 11 and the periphery of the plate has apertures through which the tie bolts pass for movably mounting the plate 17 for movement toward and away from the stationary bottom plate, thereby forming a variable volume chamber for the flexible bag B containing fluid to be ejected by applying collapsing pressure to the bag.

A threaded rod 18 parallel to the top and bottom plates 10 and 11 extends between the plates and through one housing end plate 13 and has a crank handle secured in the socket of a crank handle 19 by a set screw 20. Preferably, the rod 18 is connected medially of the end plates 13 to a coaxial rod 18' by means of a coupling sleeve 21 having set screws therein. The rods 18 and 18' have oppositely pitched screw threads, one being a right hand thread and the other being a left hand thread.

Tensioning plates 22 and 22' are mounted for axial movement on the rods 18 and 18', respectively, and the plates have spring holder sleeves 23 and 23' secured to their inner surfaces with tubular extensions 24 and 24' extending axially toward each other. The sleeves 23 and 23' are journaled on the rods 18 and 18', respectively. A tensioning spring 25 encircles the rods and extends between the plates 22 and 22', its ends being secured to the holders 23 and 23'.

A nut 26 is screwed on rod 18 between the coupling 21 and the extension sleeve 24 of spring holder 23, and a nut 26' is screwed on rod 18' between the coupling 21 and the extension sleeve 24' of spring holder 23'. A non-rotating or locking rod 28 extends slidably through the spring holders 23 and 23' laterally of the rods 18 and 18' and through notches 29 in the nuts 26 and 26' to prevent the nuts from rotating when the rods 18 and 18' are rotated.

The tensioning plates 22 and 22' have laterally opposite wings 30 and 30' extending laterally outward with laterally outer portions 31 and 31' at 90° extending longitudinally toward each other, the portions 31 being substantially longer than portions 31'. Parallelogram linkages on opposite sides of the spring 25 connect the longitudinal portions 31 and 31' with the top plate 10 and the movable pressure plate 17. As shown, the top plate 10 has depending longitudinal flanges 33 to which the linkages are connected, and the pressure plate 17 has parallel upstanding longitudinal flanges 34 to which the linkages are connected.

Each linkage comprises two pairs of angled parallel link arms 35 connected at their inner ends to pivots 36 on the longitudinal wing portions 31, and connected at their outer ends to pivots 37 and 38 on the flanges 33 and 34 of the top plate 10 and pressure plate 17. Another pair of oppositely angled parallel link arms 40 has their inner ends connected to a pivot 36' on the longitudinal wing portions 31' and their outer ends connected to the pivots 38.

Figure 3:
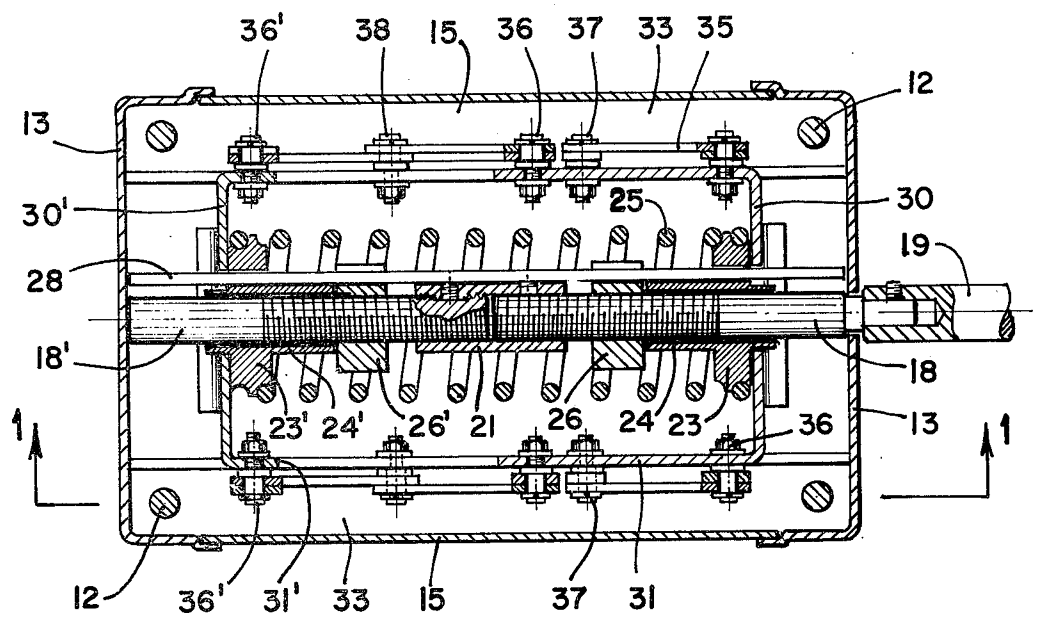
FIG. 3 is a sectional view on line 3—3 of FIG. 1.
Figure 4:
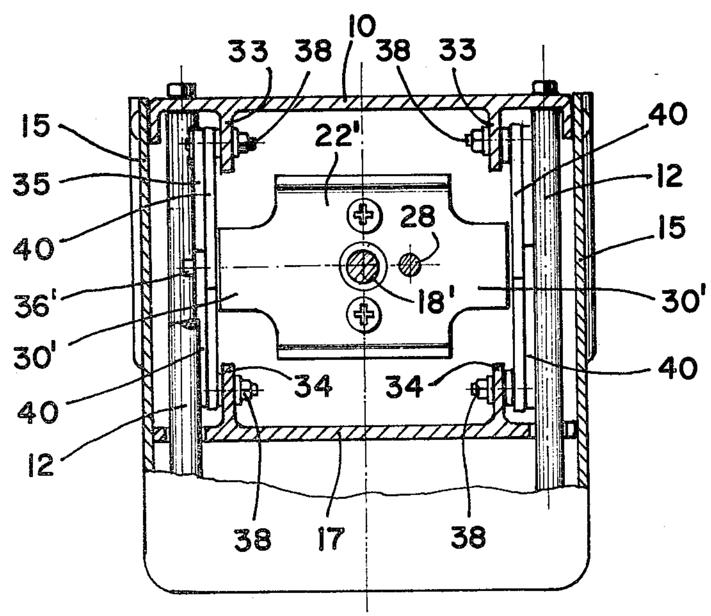
FIG. 4 is a sectional view on line 4—4 of FIG. 1.

It will be apparent that when the crank 19 is turned to rotate the rods 18 and 18' in one direction, the nuts 26 and 26' will move axially away from each other and when rotated in the opposite direction the nuts will move toward each other. When the nuts move away from each other, they move away from the coupling 21, as indicated in FIGS. 1 and 3, into abutment with the spring holder extensions 24 and 24' and move the tensioning plates 30 and 30' away from each other a corresponding amount, thus placing a tension load on the spring 25. This movement of the tensioning plates moves the pivot 36' longitudinally in one direction and the pivots 36 longitudinally in the opposite direction, causing the pressure plate 17 to move upwardly away from the bottom plate 11 to a position such as represented in FIG. 1, which allows insertion of the bag B containing fluid between the plates.

Figure 2:
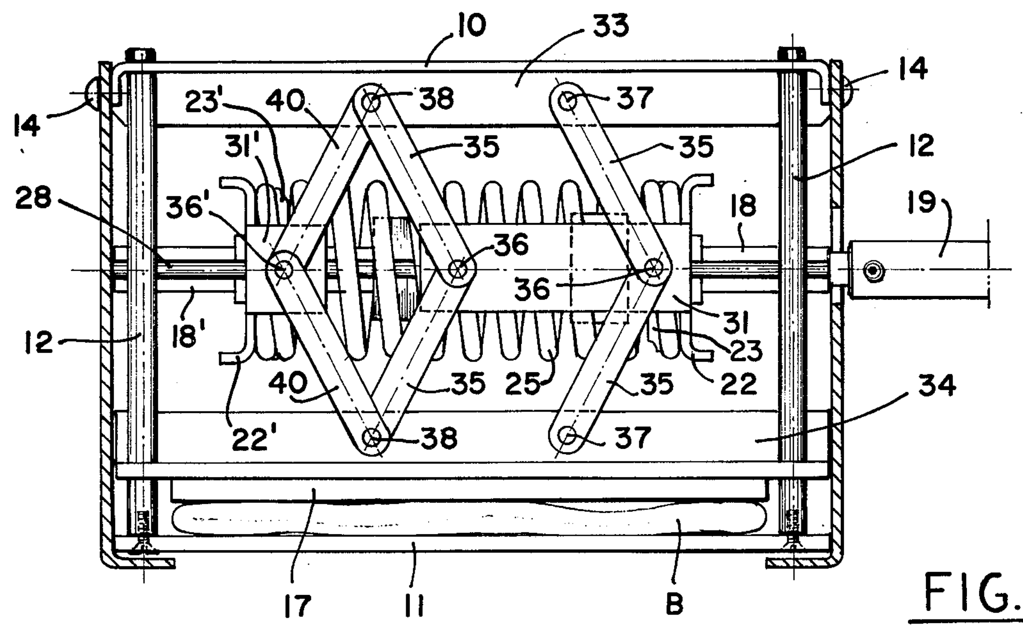
FIG. 2 is a similar view with the pressure plate moved toward the stationary plate to compress the container.

After the bag has been inserted, the crank is rotated in the reverse direction until the nuts 26 and 26' abut the coupling 21. This places the tension load of spring 25 on the tensioning plates 22 and 22', urging them toward each other. However, as they move in that direction their movement is transmitted by the linkages to the pressure plate, and the force transmitted by the linkages increases as the tension of the spring decreases so as to maintain a substantially constant pressure compressing the bag B until the bag is substantially collapsed as shown in FIG. 2, which is very desirable in injecting blood into a patient. In other words, a mechanical advantage is obtained by the linkages which compensates for the decrease in spring tension.

Moreover, the parallelogram linkages also function to maintain the plates 11 and 17 parallel at all times. The travel of the nuts is limited by the spacing between the coupling 21 and the spring holder extensions 24 and 24', which is calculated to limit the closing movement of the pressure plate to a position wherein the bag is not fully collapsed so that any air in the fluid bag is not injected into the patient.

The improved fluid pressurizing device is simple, compact and inexpensive and provides for applying substantially constant pressure to a flexible bag containing fluid to eject the fluid at a constant rate.

What is claimed is:

1. Apparatus for pressurizing a flexible fluid-containing container comprising, a frame having a stationary plate and a pressure plate movable toward and away from said stationary plate to form a variable volume chamber therebetween, a tension spring, parallelogram linkage means operatively connecting the ends of said spring to said pressure plate for transmitting the spring tension thereto and substantially compensating for reduced tension as the pressure plate moves toward said stationary plate, a screw having opposite handed threads extending axially through said spring, and nuts on said threads adapted to axially expand the spring and move the pressure plate away from the stationary plate when the screw is rotated in one direction.

2. Apparatus for pressurizing a flexible fluid-containing container as defined in claim 1, wherein means on the screw limits the movement of the nuts toward each other when the screw is reversely rotated.

3. Apparatus for pressurizing a flexible fluid-containing container as defined in claim 1, wherein tensioning plates are secured to the ends of said spring and the linkage connects the tensioning plate to the stationary plate and the pressure plate, and the nuts move the tensioning plates away from each other to expand the spring when the screw is rotated in one direction.

4. Apparatus for pressurizing a flexible fluid-containing container as defined in claim 3, wherein means on the screw limits the movement of the nuts toward each other when the screw is reversely rotated.

5. Apparatus for pressurizing a flexible fluid-containing container as defined in claim 3, wherein means extending between the tensioning plates engages the nuts to prevent rotation thereof.

* * * * *